United States Patent
Brown (10) Patent No.: US 7,998,217 B1
(45) Date of Patent: Aug. 16, 2011

(54) MODULAR OFFSET STEM IMPLANTS

(75) Inventor: David R Brown, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 1408 days.

(21) Appl. No.: 11/049,222

(22) Filed: Feb. 2, 2005

(51) Int. Cl.
*A61F 2/38* (2006.01)

(52) U.S. Cl. ............... 623/20.15; 623/20.14; 623/20.34; 623/20.36

(58) Field of Classification Search ............... 623/20.15, 623/20.34, 20.36, 19.14
See application file for complete search history.

(56) References Cited

U.S. PATENT DOCUMENTS

| | | |
|---|---|---|
| 3,534,731 A | 10/1970 | Muller |
| 3,774,244 A | 11/1973 | Walker |
| 3,868,730 A | 3/1975 | Kaufer et al. |
| RE28,841 E | 6/1976 | Allgower et al. |
| RE29,757 E | 9/1978 | Helfet |
| 4,134,158 A | 1/1979 | Laure |
| 4,167,047 A | 9/1979 | Grundei et al. |
| 4,205,400 A | 6/1980 | Shen et al. |
| 4,213,209 A | 7/1980 | Insall et al. |
| 4,219,893 A | 9/1980 | Noiles |
| 4,224,696 A | 9/1980 | Murray et al. |
| 4,224,697 A | 9/1980 | Murray et al. |
| 4,255,439 A | 3/1981 | Cooper |
| 4,301,553 A | 11/1981 | Noiles |
| 4,309,778 A | 1/1982 | Buechel et al. |
| 4,358,859 A | 11/1982 | Schurman et al. |
| 4,404,691 A | 9/1983 | Buning et al. |
| 4,495,664 A | 1/1985 | Blanquaert |
| 4,538,305 A | 9/1985 | Engelbrecht et al. |
| 4,578,081 A | 3/1986 | Harder et al. |
| 4,624,673 A | 11/1986 | Meyer |
| 4,676,797 A | 6/1987 | Anapliotis et al. |
| 4,696,290 A | 9/1987 | Steffee |
| 4,711,639 A | 12/1987 | Grundei |
| 4,713,076 A | 12/1987 | Draenert |
| 4,714,471 A | 12/1987 | Grundei |
| 4,787,907 A | 11/1988 | Carignan |
| 4,790,852 A | 12/1988 | Noiles |
| 4,790,854 A | 12/1988 | Harder et al. |
| 4,805,607 A | 2/1989 | Engelhardt et al. |
| 4,822,365 A | 4/1989 | Walker et al. |
| 4,822,366 A | 4/1989 | Bolesky |
| 4,834,758 A | 5/1989 | Lane et al. |
| 4,846,839 A | 7/1989 | Noiles |

(Continued)

FOREIGN PATENT DOCUMENTS

DE     1 575 278     9/1980

(Continued)

OTHER PUBLICATIONS

Biomet Offset Tibia; Biomet Orthopedics, Inc., Dec. 2001.

(Continued)

*Primary Examiner* — Corrine M McDermottt
*Assistant Examiner* — Christopher D Prone
(74) *Attorney, Agent, or Firm* — Harness, Dickey (57) ABSTRACT

A modular device for coupling a stem to an end component of an implant. The device includes a plurality of rotatably interconnectable intermediate components for coupling the stem to the end component, such that each intermediate component can be rotated for selectively changing a total offset between the stem and the end component by a relative offset.

25 Claims, 5 Drawing Sheets

U.S. PATENT DOCUMENTS

| | | | |
|---|---|---|---|
| 4,888,021 A | 12/1989 | Forte et al. | |
| 4,904,110 A | 2/1990 | Klein | |
| 4,936,853 A | 6/1990 | Fabian et al. | |
| 4,944,757 A | 7/1990 | Martinez et al. | |
| 4,950,297 A * | 8/1990 | Elloy et al. | 623/20.29 |
| 4,950,298 A | 8/1990 | Gustilo et al. | |
| 4,959,071 A | 9/1990 | Brown et al. | |
| 4,963,155 A | 10/1990 | Lazzeri et al. | |
| 4,985,037 A | 1/1991 | Petersen | |
| 4,995,883 A | 2/1991 | Demane et al. | |
| 5,002,578 A | 3/1991 | Luman | |
| 5,002,581 A | 3/1991 | Paxson et al. | |
| 5,007,931 A | 4/1991 | Smith | |
| 5,011,496 A | 4/1991 | Forte et al. | |
| 5,019,103 A | 5/1991 | Van Zile et al. | |
| 5,057,111 A | 10/1991 | Park | |
| 5,061,271 A | 10/1991 | Van Zile | |
| 5,061,286 A | 10/1991 | Lyle | |
| 5,062,849 A | 11/1991 | Schelhas | |
| 5,071,438 A | 12/1991 | Jones et al. | |
| 5,123,928 A | 6/1992 | Moser | |
| 5,127,914 A | 7/1992 | Calderale et al. | |
| 5,133,760 A | 7/1992 | Petersen et al. | |
| 5,133,763 A | 7/1992 | Mullers | |
| 5,137,535 A | 8/1992 | Keller | |
| 5,137,536 A | 8/1992 | Koshino | |
| 5,139,521 A | 8/1992 | Schelhaus | |
| 5,152,796 A | 10/1992 | Slamin | |
| 5,194,066 A | 3/1993 | Van Zile | |
| 5,226,915 A | 7/1993 | Bertin | |
| 5,234,431 A | 8/1993 | Keller | |
| 5,258,032 A | 11/1993 | Bertin | |
| 5,258,034 A | 11/1993 | Furlong et al. | |
| 5,269,784 A | 12/1993 | Mast | |
| 5,271,737 A | 12/1993 | Baldwin et al. | |
| 5,282,865 A | 2/1994 | Dong | |
| 5,286,253 A | 2/1994 | Fucci | |
| 5,286,260 A | 2/1994 | Bolesky et al. | |
| 5,290,288 A | 3/1994 | Vignaud et al. | |
| 5,290,313 A | 3/1994 | Heldreth | |
| 5,326,359 A | 7/1994 | Oudard | |
| 5,330,534 A | 7/1994 | Herrington et al. | |
| 5,334,184 A | 8/1994 | Bimman | |
| 5,336,225 A | 8/1994 | Zang | |
| 5,342,366 A | 8/1994 | Whiteside et al. | |
| 5,352,227 A | 10/1994 | O'Hara | |
| 5,358,526 A | 10/1994 | Tornier | |
| 5,370,701 A | 12/1994 | Finn | |
| 5,387,240 A | 2/1995 | Pottenger et al. | |
| 5,387,241 A | 2/1995 | Hayes | |
| 5,397,360 A | 3/1995 | Cohen et al. | |
| 5,405,395 A | 4/1995 | Coates | |
| 5,405,396 A | 4/1995 | Heldreth et al. | |
| 5,413,605 A | 5/1995 | Ashby et al. | |
| 5,545,228 A | 8/1996 | Kambin | |
| 5,556,433 A | 9/1996 | Gabriel et al. | |
| 5,557,433 A | 9/1996 | Gabriel et al. | |
| 5,593,449 A | 1/1997 | Roberson, Jr. | |
| 5,609,641 A | 3/1997 | Johnson et al. | |
| 5,609,642 A | 3/1997 | Johnson et al. | |
| 5,613,970 A | 3/1997 | Houston et al. | |
| 5,620,445 A * | 4/1997 | Brosnahan et al. | 606/63 |
| 5,634,927 A | 6/1997 | Houston et al. | |
| 5,643,303 A | 7/1997 | Donahue | |
| 5,645,607 A | 7/1997 | Hickey | |
| 5,658,349 A | 8/1997 | Brooks et al. | |
| 5,683,469 A | 11/1997 | Johnson et al. | |
| 5,683,470 A | 11/1997 | Johnson et al. | |
| 5,702,460 A | 12/1997 | Carls et al. | |
| 5,766,255 A | 6/1998 | Slamin et al. | |
| 5,776,200 A | 7/1998 | Johnson et al. | |
| 5,782,920 A | 7/1998 | Colleran | |
| 5,782,921 A | 7/1998 | Colleran et al. | |
| 5,800,552 A | 9/1998 | Forte | |
| 5,824,097 A | 10/1998 | Gabriel et al. | |
| 5,824,104 A | 10/1998 | Tuke | |
| 5,879,391 A | 3/1999 | Slamin | |
| 5,902,340 A | 5/1999 | White et al. | |
| 5,944,756 A | 8/1999 | Fischetti et al. | |
| 6,039,764 A | 3/2000 | Pottenger et al. | |
| 6,063,091 A | 5/2000 | Lombardo et al. | |
| 6,063,122 A | 5/2000 | O'Neil et al. | |
| 6,071,311 A | 6/2000 | O'Neil et al. | |
| 6,102,956 A * | 8/2000 | Kranz | 623/23.15 |
| 6,126,693 A | 10/2000 | O'Neil et al. | |
| 6,139,584 A | 10/2000 | Ochoa et al. | |
| 6,146,424 A * | 11/2000 | Gray et al. | 623/20.34 |
| 6,149,687 A | 11/2000 | Gray, Jr. et al. | |
| 6,162,255 A | 12/2000 | Oyola | |
| 6,171,342 B1 | 1/2001 | O'Neil et al. | |
| 6,214,052 B1 | 4/2001 | Burkinshaw | |
| 6,217,619 B1 | 4/2001 | Keller et al. | |
| 6,228,091 B1 | 5/2001 | Lombardo et al. | |
| 6,228,120 B1 | 5/2001 | Leonard et al. | |
| 6,264,699 B1 | 7/2001 | Noiles et al. | |
| 6,306,172 B1 | 10/2001 | O'Neil et al. | |
| 6,423,096 B1 | 7/2002 | Musset et al. | |
| 6,447,549 B1 | 9/2002 | Taft | |
| 6,505,387 B1 | 1/2003 | Yatskov et al. | |
| 6,506,216 B1 | 1/2003 | McCue et al. | |
| 6,613,092 B1 | 9/2003 | Kana et al. | |
| 6,663,670 B2 | 12/2003 | Rogers et al. | |
| 6,673,114 B2 | 1/2004 | Hartdegen et al. | |
| 6,706,072 B2 | 3/2004 | Dwyer et al. | |
| 6,736,852 B2 | 5/2004 | Callaway et al. | |
| 6,749,637 B1 | 6/2004 | Bahler | |
| 6,783,551 B1 | 8/2004 | Metzger et al. | |
| 6,797,006 B2 | 9/2004 | Hodorek | |
| 6,923,832 B1 | 8/2005 | Sharkey et al. | |
| 6,953,479 B2 * | 10/2005 | Carson et al. | 623/20.15 |
| 6,972,039 B2 | 12/2005 | Metzger et al. | |
| 6,986,791 B1 | 1/2006 | Metzger | |
| 7,153,326 B1 | 12/2006 | Metzger | |
| 7,468,078 B2 | 12/2008 | Sederholm et al. | |
| 2003/0014120 A1 | 1/2003 | Carson et al. | |
| 2003/0055508 A1 | 3/2003 | Metzger et al. | |
| 2003/0065397 A1 | 4/2003 | Hanssen et al. | |
| 2003/0180117 A1 | 9/2003 | Niku | |
| 2003/0204263 A1 | 10/2003 | Justin et al. | |
| 2004/0049284 A1 | 3/2004 | German et al. | |
| 2004/0162619 A1 | 8/2004 | Blaylock et al. | |
| 2004/0172137 A1 | 9/2004 | Blaylock et al. | |
| 2004/0199260 A1 | 10/2004 | Pope et al. | |
| 2005/0154470 A1 | 7/2005 | Sekel | |
| 2008/0021566 A1 | 1/2008 | Peters et al. | |

FOREIGN PATENT DOCUMENTS

| | | |
|---|---|---|
| EP | 010 527 | 4/1980 |
| EP | 0 144 667 | 5/1988 |
| EP | 0 495 340 | 7/1992 |
| EP | 0 307 655 | 8/1992 |
| EP | 0 531 263 | 3/1993 |
| EP | 0 621 019 | 10/1994 |
| EP | 0 529 408 | 12/1995 |
| FR | 2 288 509 | 5/1976 |
| FR | 2 701 387 | 8/1994 |
| GB | 2 259 253 | 3/1993 |
| GB | 2 312 168 | 10/1997 |
| WO | WO97/09939 | 3/1997 |

OTHER PUBLICATIONS

International Search Report for PCT/US2007/016148 mailed Nov. 27, 2007, claiming priority to U.S. Appl. No. 11/488,851, filed Jul. 18, 2006.

International Preliminary Report on Patentability for PCT/US2007/016148 mailed Jan. 29, 2009, claiming priority to U.S. Appl. No. 11/488,851, filed Jul. 18, 2006.

Written Opinion for PCT/US2007/016148 mailed Nov. 27, 2007, claiming priority to U.S. Appl. No. 11/488,851, filed Jul. 18, 2006.

* cited by examiner

MODULAR OFFSET STEM IMPLANTS

INTRODUCTION

Various modular stem implants are currently available for knee replacement procedures. Some tibial implants, for example, incorporate a component that provides an offset to address anatomical mismatch between the patient's intramedullary canal and the center of the proximal tibia.

Although the existing modular implants can be satisfactory for their intended purposes, modular implants that provide additional anatomical flexibility are still desirable.

SUMMARY

The present teachings provide a modular device for coupling a stem to an end component of an implant. The device includes a plurality of rotatably interconnectable intermediate components for coupling the stem to the end component, such that each intermediate component can be rotated for selectively changing a total offset between the stem and the end component by a relative offset.

The present teachings also provide a modular device for coupling a stem to an end component of an implant, and including a first component rotatably coupled to the end component at a first relative offset, and a second component rotatably coupled to the stem at a second relative offset, wherein the first and second components are rotatably coupled therebetween.

The present teachings further provide a modular implant that includes an end component, a stem, and a plurality of rotatably interconnectable intermediate components for coupling the stem to the end component, and providing at least two relative offsets.

The present teachings also provide a modular implant that includes an end component having a center axis, a stem having a stem axis, and a plurality of rotatably interconnectable intermediate components coupling the stem to the end component, such that the center axis and the stem axis can be selectively offset relative to one another by a total offset within a predetermined range.

The present teachings provide a method for coupling a stem to an end component of a modular implant. The method includes providing a plurality of modular intermediate components, wherein at least two components of the group comprising the end component and the intermediate components are configured for eccentric coupling, sequentially coupling the plurality of intermediate components between the end component and the stem, and selectively rotating at least one intermediate component to change a total offset between the stem and the end component.

Further areas of applicability of the present invention will become apparent from the detailed description provided hereinafter. It should be understood that the detailed description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION

The following description is merely exemplary in nature and is in no way intended to limit the invention, its application, or uses. For example, although the present teachings are illustrated for tibial implants in knee surgery, the present teachings can be used for any other orthopedic procedures that require implants that include a stem received in a long bone, such as, for example, femoral implants and shoulder implants.

Figure 1:
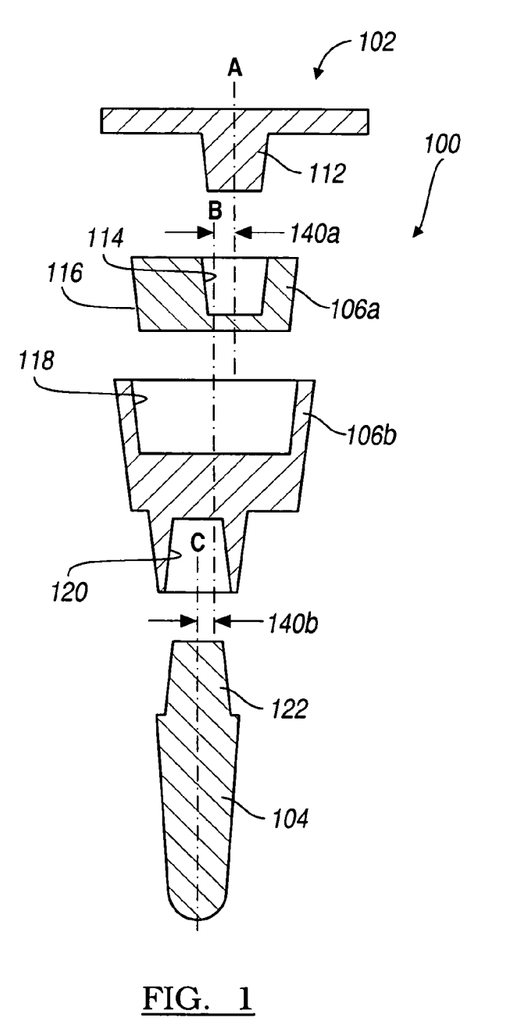
FIG. 1 is an exploded sectional view of a modular implant according to the present teachings.
Figure 1A:
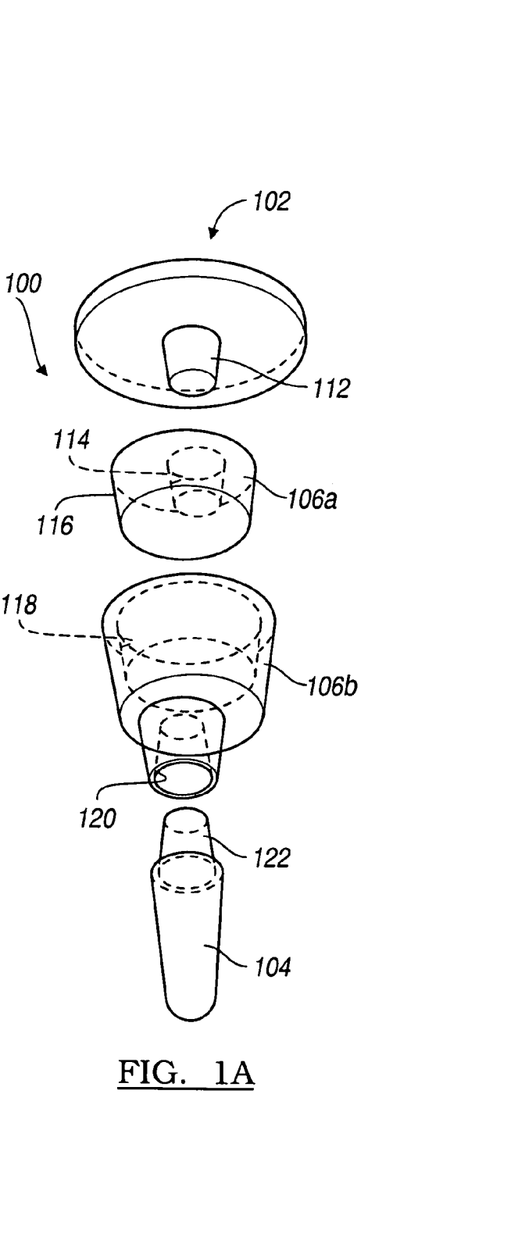
FIG. 1A is an exploded isometric view of a modular implant according to the present teachings.
Figure 1B:
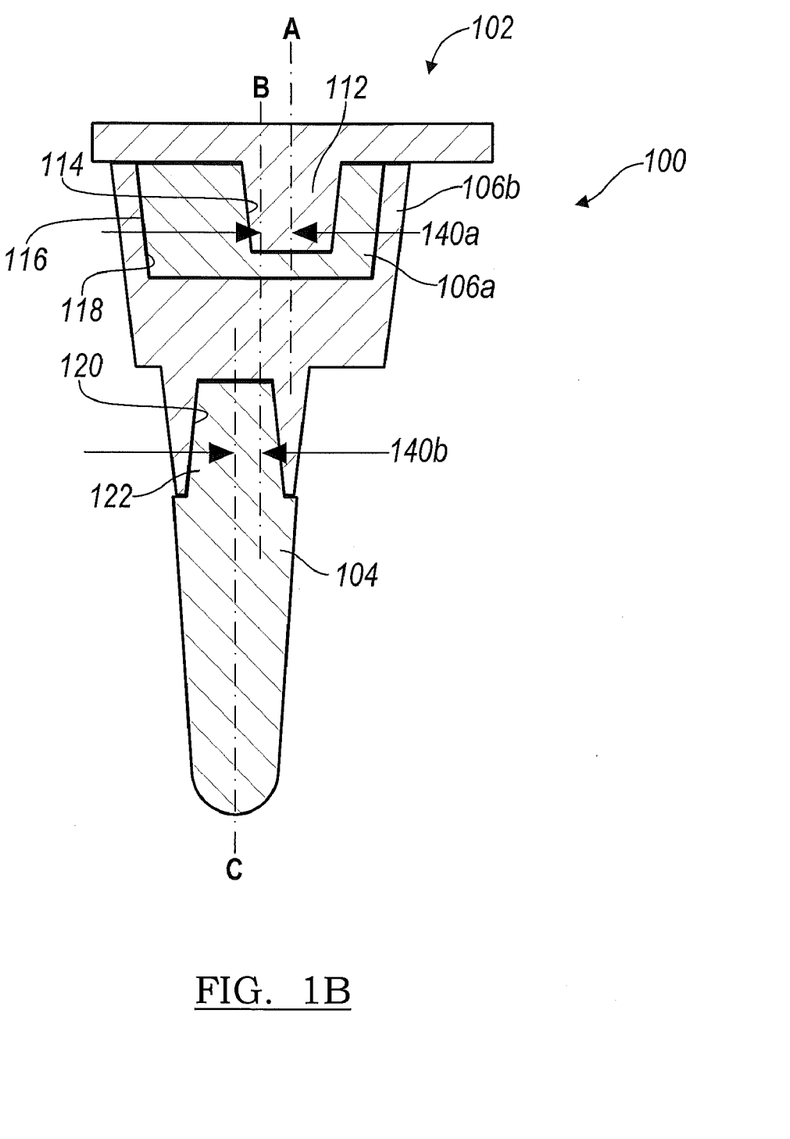
FIG. 1B is an assembled view of the modular implant shown in exploded view in FIG. 1.
Figure 2:
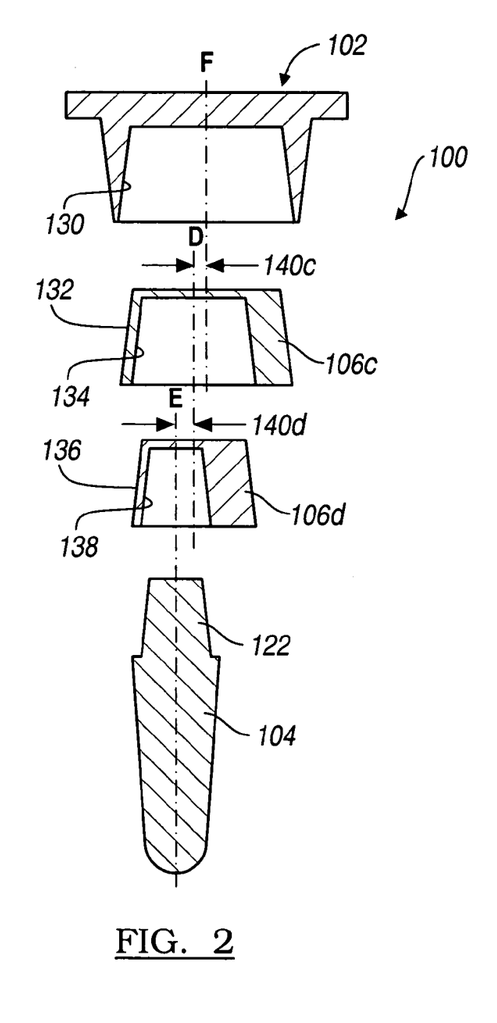
FIG. 2 is an exploded sectional view of a modular implant according to the present teachings.

Referring to FIGS. 1, 1A and 2, an exemplary modular implant 100 according to the present teachings includes an end component 102 and a stem 104. Although the end component 102 is illustrated as a tibial tray for a proximal tibial implant, the end component 102 can also be a body or neck or trunnion for a distal femoral implant, or an end component for a humeral implant.

The end component 102 can be coupled with the stem 104 by a plurality of modular intermediate components 106, such as those indicated by reference numbers 106a-106d in FIGS. 1 and 2. It will be appreciated that although two intermediate components 106 are illustrated in each of the implants of FIGS. 1 and 2, a greater number of intermediate components 106 can be used. Adjacent intermediate components 106 can be coupled to one another or to the stem 104 or to the end component 102 by Morse taper or taper lock connections in various combinations of male/female tapers or other type of appropriate connections.

Referring to FIG. 1, for example, the end component 102 can include a male taper 112, which can be received in a female taper 114 of the first intermediate component 106a. The first intermediate component 106a can also include a male taper 116, which can be received in a female taper 118 of the second intermediate component 106b. The second intermediate component 106b can also include another female taper 120 which can receive a male taper 122 of the stem. The second intermediate component 106b can be constructed as an integral adapter having the two taper locks 118, 120 sequentially positioned along a longitudinal direction defined by the implant 100, as shown in FIG. 1, or as two distinct components modularly coupled.

Referring to FIG. 2, the end component 102 can include a female taper 130, which receives a male taper 132 of the first intermediate component 106c. The first intermediate component 106c can also include a female taper 134, which can receive a male taper 136 of the second intermediate component 106d. The second intermediate component 106d can also include a female taper 138 which can receive the male taper 122 of the stem. In this aspect, each intermediate component 106c, 106d can include both male and female tapers, 132, 134, and 136, 138, with the female tapers 134, 138 defined in interior surfaces of the respective male tapers 132, 136.

Referring to FIGS. 1 and 2, the modular intermediate components 106a, 106b, and 106c, 106d and the end component 102 can be selectively structured for eccentric coupling that provides at least two relative offsets 140, such as first and second relative offsets 140a, 140b, and 104c, 140d for the corresponding implants 100 shown in FIGS. 1 and 2. It will be appreciated that when more than two additional intermediate components 106 are coupled between the end component 102 and the stem 104, additional relative offsets 140 can be provided, as desired. The relative offsets 140 of the implant 100 can be all of equal size (width) or can have variable sizes. Further, the relative offsets 140 can be all oriented toward a single direction (unilateral) to provide a total offset that is the sum of the relative offsets or can have variable orientations (multilateral) resulting in a total offset of 0 or less than the sum of the relative offsets as described below. Because of the taper lock connections, the orientation of each intermediate component can be readily changed by rotation. Once a desired orientation is selected, that particular orientation can be secured by using self-locking tapers or various methods and devices known in the art, such as, for example, screws, washers or other locking devices.

Referring to FIG. 1, the first relative offset 140a can be formed, for example, by offsetting center axes A and B of the female tapers 114, 118 of the first and second intermediate components 106a, 106b, respectively. It will be appreciated that in the exemplary illustration of FIG. 1, the axis B is also the axis of the male taper 116 and the first intermediate component 106a is structured for eccentric coupling by including eccentrically arranged female and male tapers 114, 116. The second relative offset 140b can be defined by offsetting center axes B and C of the female tapers 118 and 120 of the second intermediate component 106b.

Referring to FIG. 2, the first relative offset 140c can be defined, for example, by offsetting a center axis F of the female taper 130 of the end component 102 from a center axis D of the female taper 134 of the first intermediate component 106a. The second relative offset 140d can be defined by offsetting center axes D and E of the female tapers 134 and 138 of the first and second intermediate components 106c, 106d respectively. As illustrated in FIG. 2, each the first and second intermediate component 106c, 106d include female and male tapers that are offset, such that the first and second intermediate component 106c, 106d are configured for eccentric coupling. It is further noted that the axis F is also the center axis of the male taper 132 of the first intermediate component 106c, and that the axis D is also the center axis of the male taper 136 of the second intermediate component.

It should be appreciated that the number, arrangement and orientation of the intermediate components 106 can be varied to achieve a total offset of desired width and orientation between the end component 102 and the stem 104. The total offset is the result of relative offsets 140, such as those illustrated by reference numerals 140a, 140b, 140c, 140d in FIGS. 1 and 2. For example, each relative offset 140a, 140b can be 2.5 mm in width, for a total offset of 5 mm when the relative offsets 140a, 140b are unilaterally arranged, as shown in FIG. 1. The same relative offsets 140a, 140b can be arranged in opposite directions, 180° apart, to provide a total offset of 0 mm, or at two directions defining other angles, to provide a 2.5 mm offset in each of those directions. Similarly, the relative offsets 140 can be unequal. For example, the offset 140c can be 2.5 mm and the offset 140d can be 1 mm, providing a total offset of 3.5 mm for unilaterally arranged offsets, and 1.5 mm for opposing offsets. The relative offsets 140 can be created by offsetting the center axes of the male and/or female tapers of adjacent components 106 relative to one another or between an intermediate component 106 and the end component 102 or the stem 104. Further, the relative offsets can be arranged at infinite rotational directions (360°) about the stem 104, can be indexable, or can be directionally fixed by adding a key to the corresponding taper lock connections.

Figure 3:
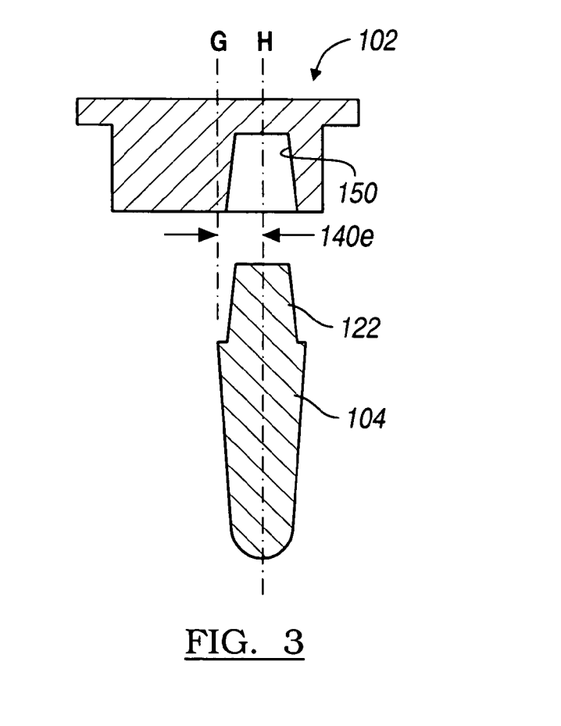
FIG. 3 is an exploded sectional view of a configuration of a modular implant according to the present teachings.

Referring to FIG. 3, in one aspect, the end component 102 can include an eccentric female taper 150 that provides an offset 140e between a center axis G of the end component 102 and a center axis H of the female taper 150. The end component 102 can be selectively coupled either directly to the stem component 104, as shown in FIG. 3, or indirectly by using appropriately sized intermediate components 106, such as those illustrated in FIG. 2.

Figure 4:
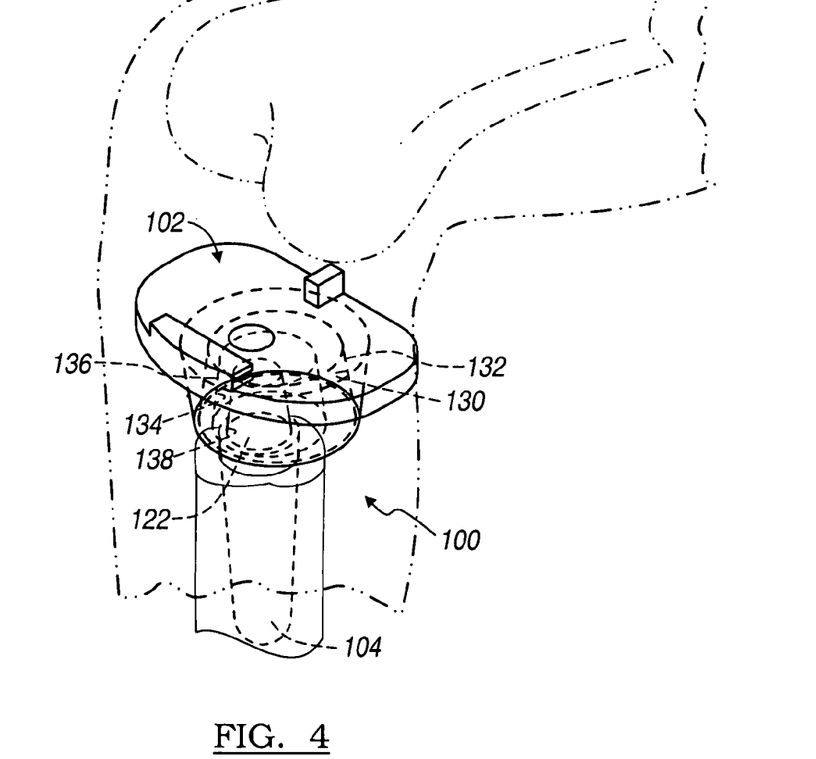
FIG. 4 is a perspective environmental view of a modular implant according to the present teachings.
Figure 5A:
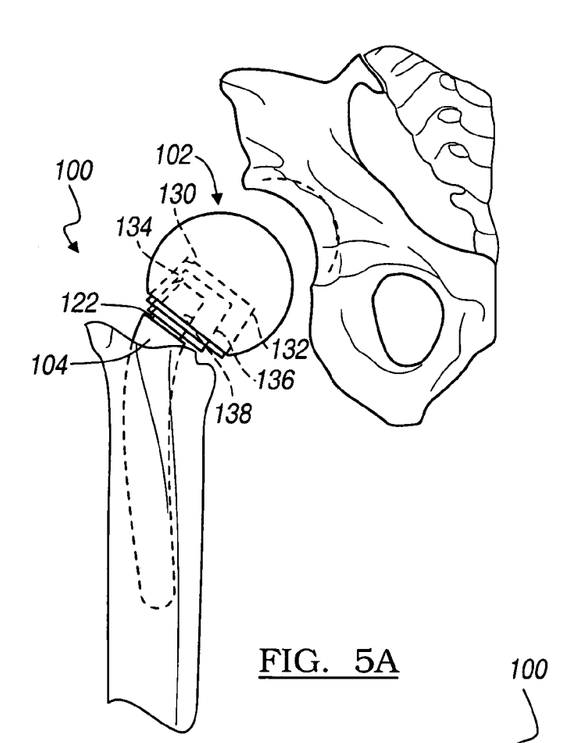
FIGS. 5A and 5B are perspective environmental views of a modular implant according to the present teachings.
Figure 5B:
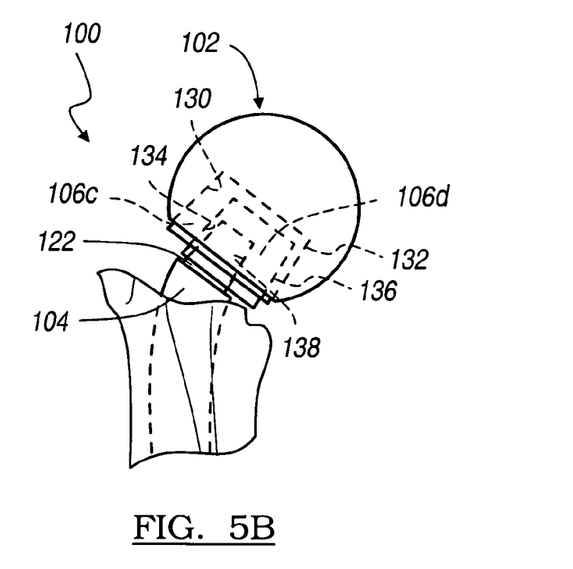

Referring to FIGS. 4, 5A and 5B, various exemplary environmental views of the modular implant 100 are illustrated. In FIG. 4, the modular implant 100 are shown implanted in the tibia of a knee. In FIG. 5A, the modular implant 100 is shown in hip replacement. In FIG. 5B, the modular implant 100 is shown generally implanted into a long bone.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A modular device for coupling a stem to an end component of an implant, the device comprising:
   a plurality of rotatably interconnectable intermediate components for coupling the stem to the end component, the plurality of intermediate components including a first component having a tapered outer surface, the outer surface having an outer diameter greater than a height of the outer surface, and a second component having first and second female tapers and a piecewise tapered outer surface, wherein the first component is received entirely within the second component, the plurality of intermediate components defining at least first and second relative offsets, such that at least one intermediate component can be rotated for selectively changing a total offset between the stem and the end component by changing the orientation of at least one of the first and second relative offsets.

2. The modular device of claim 1, wherein the intermediate components are coupled with taper lock connections.

3. The modular device of claim 1, wherein the first and second relative offsets are equal in size.

4. The modular device of claim 1, wherein the first and second relative offsets have unequal sizes.

5. The modular device of claim 1, wherein the first and second relative offsets have different orientations.

6. The modular device of claim 1, wherein the first and second female tapers of the second component are offset relative to one another along a longitudinal direction.

7. The modular device of claim 1, wherein the first relative offset is defined between a center axis of the first component and a center axis of the end component.

8. The modular device of claim 1, wherein the second relative offset is defined between the second component and the stem.

9. A modular device for coupling a stem to an end component of an implant, the device comprising:
   a first component having a first female taper rotatably coupled to a male taper of the end component at a first relative offset, the first component having a tapered outer surface, the outer surface having a diameter greater than a height of the outer surface; and
   a second component having a second female taper rotatably coupled to a male taper of the stem at a second relative offset, the second relative offset unequal in size than the first relative offset, the second component having a third female taper rotatably receiving the first component entirely therewithin for selectively changing a total offset between the end component and the stem, the second component having a piecewise tapered outer surface.

10. The modular implant of claim 9, wherein the first and second relative offsets are unilaterally additive.

11. The modular device of claim 9, wherein the second and third female tapers of the second component are offset relative to one another along a longitudinal direction.

12. The modular device of claim 9, wherein the first female taper of the first component has a center axis offset from a center axis of the tapered outer surface.

13. A modular implant comprising:
an end component having a tibial tray and a male taper extending from the tibial tray;
a stem having a male taper;
a first component having a female taper rotatably coupled to the male taper of the end component at a first relative offset, the first component having a tapered outer surface, the outer surface having an outer diameter greater than a height of the outer surface perpendicular to the diameter; and
a second component including a first portion having an outer tapered surface and a first female taper, the first portion having an outer diameter greater than a height of the first female taper and a second portion integrally extending from the first portion, the second portion having a tapered outer surface and a second female taper, the first female taper of the second component rotatably receiving the first component entirely therewithin, the second female taper of the second component rotatably receiving the male taper of the stem component at a second relative offset, wherein the first and second offsets can be selectively oriented in different orientations relative to one another for changing the total offset between the end component and the stem.

14. The modular implant of claim 13, wherein the first and second relative offsets are equal in size.

15. The modular implant of claim 13, wherein the first and second relative offsets have unequal sizes.

16. The modular implant of claim 13, wherein the first and second relative offsets have different orientations.

17. The modular implant of claim 13, wherein the end component is a tibial tray or a femoral component or a humeral component.

18. A modular implant comprising:
an end component having a center axis, a tibial tray and an end male taper extending from the tibial tray;
a stem having a stem axis and a stem male taper; and
at least first and second rotatably interconnectable intermediate components coupling the stem to the end component, such that the center axis and the stem axis can be selectively offset relative to one another by a total offset within a predetermined range, the total offset including at least a first relative offset of the first intermediate component relative to the center axis and a second relative offset of the second intermediate component relative to the stem axis, the first relative offset unequal in size than the second relative offset, the predetermined range including a maximum offset and a minimum offset, and wherein the first intermediate component has an outer diameter greater than a height of the first intermediate component, the first intermediate component including a female taper receiving the end male taper of the end component, the first intermediate component received entirely within a first female taper of the second intermediate component, and the second intermediate component having a piecewise tapered outer surface and a second female taper receiving the stem male taper.

19. The modular implant of claim 18, wherein the maximum offset includes a sum of the first and second relative offsets, the first and second relative offsets having a unilateral orientation.

20. The modular implant of claim 19, wherein the minimum offset is the difference of the first and second relative offsets, the first and second relative offsets having opposite orientations.

21. The modular implant of claim 18, wherein the minimum offset is nonzero and the first and second relative offsets have different orientations.

22. A modular implant comprising:
an end component having an end connection;
a stem having a stem connection;
a first component including first and second connections, the first and second connections having first and second longitudinal axes parallel to one another and defining a first offset therebetween, the first connection rotatably coupled to the end connection, the first component having an outer diameter greater than a height of the first component; and
a second component including third and fourth connections, the third and fourth connections having third and fourth longitudinal axes parallel to one another and defining a second offset therebetween, the first and second offsets unequal in size, the third connection rotatably coupled to the second connection, the fourth connection rotatably coupled to the stem connection, such that the first and second offsets can be selectively oriented in different orientations relative to one another for changing the total offset between the end component and the stem, wherein the first connection is a female taper, the second connection is a male taper defined by an outer surface of the first component, the third connection is a female taper, and wherein the first component is received entirely within the second component, the second component having a piecewise tapered outer surface.

23. A modular implant comprising:
an end component having an end connection;
a stem having a stem connection;
a first component including first and second connections, the first and second connections having first and second longitudinal axes defining a first offset therebetween, the first connection rotatably coupled to the end connection, the first component having an outer diameter greater than a height of the first component; and
a second component including third and fourth connections, the third and fourth connections having third and fourth longitudinal axes defining a second offset therebetween, the third connection rotatably coupled to the second connection, the fourth connection rotatably coupled to the stem connection, the first and second offsets being equal in size, such that the first component can be selectively oriented relative to the second component in first and second orientations, wherein in the first orientation the first and second offsets are diametrically opposite and produce a zero total offset between the end component and the stem, and in the second orientation the first and second offsets are unilaterally oriented and produce a maximum total offset, wherein the first connection is a female taper, the second connection is a male taper defined by an outer surface of the first component, the third connection is a female taper, and wherein the first component is received entirely within the second component, the second component having a piecewise tapered outer surface.

24. The modular implant of claim 23, wherein the first and second axes are parallel to one another.

25. The modular implant of claim 23, wherein the third and fourth axes are parallel to one another.

* * * * *